United States Patent [19]

Böhm et al.

[11] Patent Number: 5,371,300

[45] Date of Patent: Dec. 6, 1994

[54] CHLORO-(2-HALOGENO-1-FLUOROMETHYL-ETHOXY)-METHANES AND THEIR PREPARATION

[75] Inventors: Stefan Böhm, Köln; Albrecht Marhold, Leverkusen, both of Germany

[73] Assignee: Bayer Aktiengesellschaft, Leverkusen, Germany

[21] Appl. No.: 145,433

[22] Filed: Oct. 29, 1993

[30] Foreign Application Priority Data

Nov. 6, 1992 [DE] Germany .............................. 4237556

[51] Int. Cl.$^5$ ............................................. C07C 43/12
[52] U.S. Cl. ..................................... 568/684; 568/683
[58] Field of Search ..................................... 568/684

[56] References Cited

PUBLICATIONS

Aliphatic Compounds, vol. 73, 1970, p. 325, 98333, "Alkoxyethyl Ethers of Hydroxymethyl Tert-Alkyl Peroxides"; Batog, et al.

*Primary Examiner*—Howard T. Mars
*Attorney, Agent, or Firm*—Sprung Horn Kramer & Woods

[57] ABSTRACT

The present invention relates to novel chloro-(2-halogeno-1-fluoromethyl-ethoxy)-methanes and to their preparation. The novel compounds can be used as intermediates for the preparation of biologically active substituted benzimidazoles.

3 Claims, No Drawings

CHLORO-(2-HALOGENO-1-FLUOROMETHYL-ETHOXY)-METHANES AND THEIR PREPARATION

The present invention relates to novel chloro-(2-halogeno-1-fluoromethyl-ethoxy)-methanes and to their preparation from the corresponding halogenated isopropanols. The novel compounds are suitable for the preparation of biologically active substituted benzimidazoles.

It is known that it is possible to chloromethylate isopropanol and thus to prepare chloro-1-methyl-ethoxymethanes (see C.A. 73 (19): 98332 q). If the methyl groups of the isopropanol have been replaced with $CH_2Hal$ groups, it is to be expected that the electronegative halogen atoms will reduce the reactivity of the OB group in comparison with halogen-free isopropanol, and that chloro-(2-halogeno-1-fluoromethyl-ethoxy)-methanes will therefore be unobtainable or obtainable only with great difficulty.

Chloro-(2-halogeno-1-fluoromethyl-ethoxy)-methanes of formula (I):

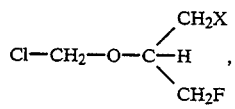    (I)

in which

X is fluorine or chlorine, have now been found.

Specifically, these compounds are chloro-(2-fluoro-1-fluoromethyl-ethoxy)-methane (formula (I), X=fluorine) and chloro-(2-chloro-1-fluoromethyl-ethoxy)-methane (formula (I), X=chlorine).

The process according to the invention for the preparation of compounds of formula (I) is characterised in that halogenated isopropanols of formula (II):

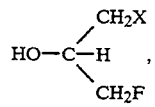    (II)

in which

X is fluorine or chlorine, are reacted with formaldehyde and hydrogen chloride at −20° to +20° C.

Halogenated isopropanols of formula (II) are known compounds (see J. Chem. Soc. 1958, 2251).

Preferred reaction temperatures for the process according to the invention are in the range −10° to ±0° C.

The process according to the invention can be carried out in the presence of solvents, for example in the presence of hydrocarbons or halogenated hydrocarbons which are liquid at the reaction temperature, although it is preferably carried out without the addition of solvents.

The formaldehyde can be used in a variety of forths, for example as paraformaldehyde. 0.8 to 1.5 mol of formaldehyde, for example, can be used per mol of a compound of formula (II). It is preferable to use 1.0 to 1.2 mol of formaldehyde per mol of a compound of formula (II).

The hydrogen chloride is preferably used in gaseous form. An example of a possible procedure is to introduce gaseous hydrogen chloride into a mixture of a compound of formula (II) and formaldehyde or paraformaldehyde, at the reaction temperature, until the reaction mixture forms two clear phases.

The reaction mixture can be worked up e.g. by separating off the organic phase, drying it and subjecting it to fractional distillation, preferably under vacuum.

It is possible in this way to obtain compounds of formula (I) in yields of well over 50%. This is extremely surprising in view of the conditions- described at the outset (the greatly reduced reactivity of the OH group which is to be expected from the introduction of halogenomethyl groups into the isopropanol).

An example of a possible procedure for the preparation of biologically active substituted benzinidazoles is to react compounds of formula (I) with a benzimidazole derivative of formula (III):

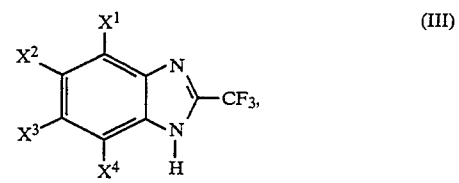    (III)

in which $X^1$, $X^2$, $X^3$ and $X^4$ independently of one another are each hydrogen, halogen, cyano or nitro, alkyl, alkoxy, alkylthio, alkylsulphinyl, alkylsulphonyl or cycloalkyl, each of which is optionally substituted fused dioxyalkylene which is optionally substituted hydroxycarbonyl, alkylcarbonyl, alkoxycarbonyl or cycloalkoxycarbonyl, amino or aminocarbonyl, each of which is optionally substituted, or aryl, aryloxy, arylthio, arylsulphinyl, arylsulphonyl, arylsulphonyloxy, arylcarbonyl, aryloxycarbonyl, arylazo or arylthiomethylsulphonyl, each of which is optionally substituted at least one of the substituents $X^1$, $X^2$, $X^3$, or $X^4$ being halogenoalkyl with the exception of the chloromethyl radical, halogenoalkoxy, halogenoalkylthio, halogenoalkylsulphinyl, halogenoalkylsulphonyl or alkylsulphonyl, fused dioxyalkylene which is optionally substituted, hydroxycarbonyl, alkylcarbonyl, alkoxycarbonyl or cycloalkoxycarbonyl, amino or aminocarbonyl, each of which is optionally substituted, or aryl, arylthio, arylsulphinyl, arylsulphonyl, arylsulphonyloxy, arylcarbonyl, aryloxycarbonyl, arylazo or arylthiomethylsulphonyl, each of which is optionally substituted, to give substituted benzimidazoles of formula (IV):

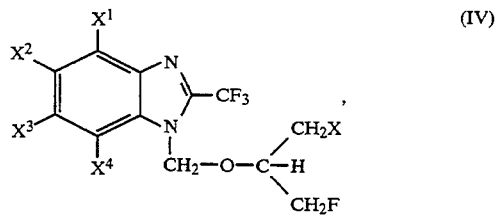    (IV)

in which

X is fluorine or chlorine and $X^3$ to $X^4$ are as defined for formula (III).

In formulae (III) and (IV), $X^1$ to $X^4$ independently of one another are each preferably hydrogen, fluorine, chlorine, bromine, iodine, cyano or nitro, alkyl, alkoxy, alkylthio, alkylsulphinyl or alkylsulphonyl, each of which is linear or branched and has 1 to 8 carbon atoms, cycloalkyl having 3 to 8 carbon atoms, halogenoalkyl, halogenoalkoxy, halogenoalkylthio, halogenoalkylsulphinyl or halogenoalkylsulphonyl, each of which is linear or branched and has 1 to 6 carbon atoms and 1 to 13 identical or different halogen atoms, or doubly linked dioxyalkylene which has 1 to 5 carbon atoms and is optionally monosubstituted or polysubstituted by identical or different substituents consisting of halogen and/or linear or branched alkyl having 1 to 4 carbon atoms and/or linear or branched halogenoalkyl having 1 to 4 carbon atoms and 1 to 9 identical or different halogen atoms, or else hydroxycarbonyl, or alkylcarbonyl or alkoxycarbonyl, each of which is linear or branched and has 1 to 6 carbon atoms in the alkyl moiety, cycloalkoxycarbonyl having 3 to 8 carbon atoms in the cycloalkyl moiety, or amino or aminocarbonyl, each of which is optionally monosubstituted or polysubstituted by identical or different substituents, the following being suitable in each case as amino substituents: alkyl having 1 to 6 carbon atoms, halogenoalkyl having 1 to 6 carbon atoms and 1 to 13 halogen atoms, or alkoxyalkyl or alkylcarbonyl each having 1 to 6 carbon atoms in the individual alkyl moieties, each of said amino substituents being linear or branched, or arylcarbonyl, arylsulphonyl, arylaminocarbonyl or arylmethylsulphonyl, each of which has 6 to 10 carbon atoms in the aryl moiety and is optionally monosubstituted or polysubstituted in the aryl moiety by identical or different substituents, it being possible for any aryl substituents present to be one or more identical or different halogens and/or linear or branched alkyl having 1 to 6 C atoms and/or linear or branched halogenoalkyl having 1 to 6 C atoms and 1 to 13 identical or different halogens, and aryl preferably being phenyl; or else aryl, aryloxy, arylthio, arylsulphinyl, arylsulphonyl, arylsulphonyloxy, arylcarbonyl, aryloxycarbonyl, arylthiomethylsulphonyl or arylazo, each of which has 6 to 10 carbon atoms in the aryl moiety and is optionally monosubstituted or polysubstituted in the aryl moiety by identical or different substituents, suitable aryl substituents being those mentioned above, and aryl preferably being phenyl, and at least one of the substituents $X^1$, $X^2$, $X^3$ or $X^4$ being halogenoalkyl (with the exception of the chloromethyl radical), halogenoalkoxy, halogenoalkylthio, halogenoalkylsulphinyl or halogenoalkylsulphonyl, each of which is linear or branched and has 1 to 6 carbon atoms and 1 to 13 identical or different halogen atoms, linear or branched alkylsulphonyl having 1 to 6 carbon atoms, or doubly linked dioxyalkylene which has 1 to 5 carbon atoms and is optionally monosubstituted or polysubstituted by identical or different substituents consisting of halogen and/or linear or branched alkyl having 1 to 4 carbon atoms and/or linear or branched halogenoalkyl having 1 to 4 carbon atoms and 1 to 9 identical or different halogen atoms, or else hydroxycarbonyl, or alkylcarbonyl or alkoxycarbonyl, each of which is linear or branched and has 1 to 6 carbon atoms in the alkyl moiety, cycloalkoxycarbonyl having 3 to 8 carbon atoms in the cycloalkyl moiety, or amino or aminocarbonyl, each of which is optionally monosubstituted or polysubstituted by identical or different substituents, the following being suitable in each case as amino substituents:

alkyl having 1 to 6 carbon atoms, halogenoalkyl having 1 to 6 carbon atoms and 1 to 13 halogen atoms, or alkoxyalkyl or alkylcarbonyl each having 1 to 6 carbon atoms in the individual alkyl moieties, each of said amino substituents being linear or branched, or arylcarbonyl, arylsulphonyl, arylaninocarbonyl or arylmethylsulphonyl, each of which has 6 to 10 carbon atoms in the aryl moiety and is optionally monosubstituted or polysubstituted in the aryl moiety by identical or different substituents, suitable aryl substituents being those mentioned above, and aryl preferably being phenyl; or else aryl, arylthio, arylsulphinyl, arylsulphonyl, arylsulphonyloxy, arylcarbonyl, aryloxycarbonyl, arylthiomethylsulphonyl or arylazo, each of which has 6 to 10 carbon atoms in the aryl moiety and is optionally monosubstituted or polysubstituted in the aryl moiety by identical or different substituents, suitable aryl substituents being those mentioned above, and aryl preferably being phenyl.

Particularly preferably, in formulae (III) and (IV),
$X^1$ is hydrogen,
$X^2$ is $CF_3$ or $OCF_3$,
$X^3$ is chlorine or $OCF_3$ or
$X^2$ and $X^3$ together are $-O-CF_2-O-$, $-O-CF_2-CF_2-O-$ or $-O-CF_2-CHF-O-$ and
$X^4$ is hydrogen.

Some of the benzimidazoles of formula (III) are known (see J. Am. Chem. Soc. 75, 1292 (1953), and U.S. Pat. specification No. 3 576 818). Benzimidazoles of formula (III) containing dioxole groupings of the type

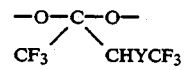

where Y=H or Hal, can be obtained for example by reacting appropriate dihydroxybenzenes with 1,1,1,4,4,4-hexafluorobut-2-enes of formula (V):

in which
$Y^1$ is H or halogen and
$Y^2$ is halogen, in the presence of a base and a diluent, at $-20°$ to $+200°$ C.

Substituted benzonidazoles of formula (IV) are suitable for example for controlling animal pests such as arthropods and nematodes, especially insects and arachnids, which occur in agriculture, in forests, in the protection of stored products and materials and in the hygiene sector. They are effective against species of normal sensitivity and resistance and against all or individual stages of development.

The preparation of substituted benzimidazoles of formula (IV), such benzimidazoles as substances, pesticides containing them, their preparation, benzimidazoles of formula (III) containing dioxole groups of the type

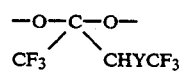

EXAMPLE 66 g of paraformaldehyde (finely powdered) were added to 192 g of 1,3-difluoropropan-2-ol. A strong stream of hydrogen chloride gas was then passed in at −10° C., with stirring, until a clear 2-phase mixture had formed. The organic phase was then separated off, dried over calcium chloride and subjected to fractional distillation under vacuum to give 183 g (60% of theory) of chloro-(2-fluoro-fluoromethyl-ethoxy)-methane with a boiling point of 50° to 54° C. at 20 mbar. The characteristic absorptions in the NMR spectra were as follows:

$^1$H NMR: 5.6 ppm and 4.55 ppm.

$^{19}$F NMR: −233 ppm.

What is claimed is:

1. Chloro-(2-halogeno-1-fluoromethyl-ethoxy)-methanes of formula (I)

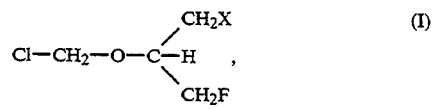

in which

X represents fluorine or chlorine.

2. Chloro-(2-fluoro-1-fluoromethyl-ethoxy)-methane.

3. Chloro-(2-chloro-1-fluoromethyl-ethoxy)-methane.

* * * * *